US006723111B2

(12) United States Patent
Abulhaj et al.

(10) Patent No.: US 6,723,111 B2
(45) Date of Patent: Apr. 20, 2004

(54) LANCET NEEDLE ANCHOR METHOD

(75) Inventors: Ramzi F. Abulhaj, Miramar, FL (US); Erol Celikoglu, Aventura, FL (US)

(73) Assignee: Vital Care Group, Inc., FL (US)

( * ) Notice: Subject to any disclaimer, the term of this patent is extended or adjusted under 35 U.S.C. 154(b) by 0 days.

(21) Appl. No.: 10/408,285

(22) Filed: Apr. 9, 2003

(65) Prior Publication Data

US 2004/0039408 A1 Feb. 26, 2004

Related U.S. Application Data

(62) Division of application No. 10/223,141, filed on Aug. 19, 2002, now Pat. No. 6,589,261.

(51) Int. Cl.[7] .............................................. A61B 17/32
(52) U.S. Cl. ..................... 606/181; 606/182; 76/119
(58) Field of Search ................................. 606/181, 182, 606/183, 167, 185; 30/342, 343; 76/119; 264/645, 537; 425/577

(56) References Cited

U.S. PATENT DOCUMENTS 3,358,689 A * 12/1967 Higgins
5,100,427 A * 3/1992 Crossman et al. .......... 606/182
5,207,699 A * 5/1993 Coe ............................ 606/182
5,385,571 A * 1/1995 Morita ........................ 606/181

OTHER PUBLICATIONS

Pamphlet describing the use of a lancet holder and lancet. ProCare LLC of Miami, Florida, U.S.A. 2002 (2 pages).

* cited by examiner

*Primary Examiner*—Michael H. Thaler
(74) *Attorney, Agent, or Firm*—H. Jay Spiegel

(57) ABSTRACT

A lancet body 15 is molded around a needle or blade, in which the inner end of the needle body which is unsharpened has an L-shape bend at the unsharpened end. The bend, when embedded in the plastic which forms the body of the lancet, secures the needle against removal. The method involves the bending substantially perpendicularly of the unsharpened end of the lancet needle or blade to be substantially perpendicular with the elongate body of the blade. The needle or blade is placed within a jig interiorly of the plastic mold. The jig includes spaced opposed clamps and a single orienting support to the bent portion of the needle. The body of the lancet is relieved in many areas to reduce material cost and has a molded tab cover eliminating a loose part such as a separate cover.

19 Claims, 4 Drawing Sheets

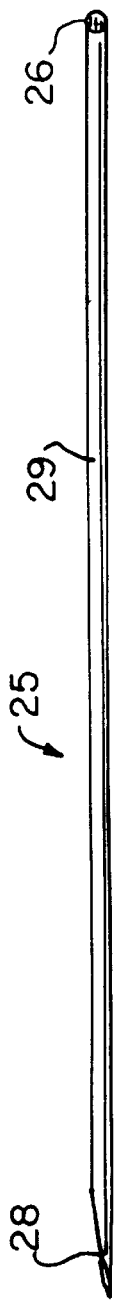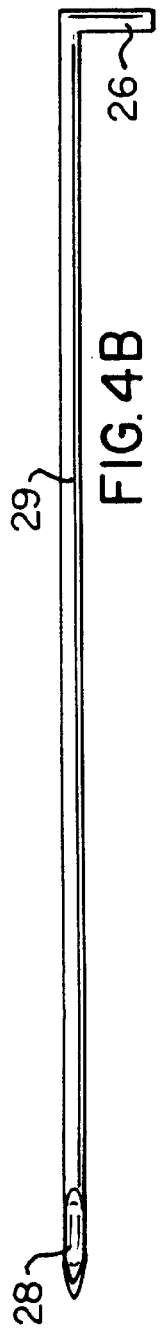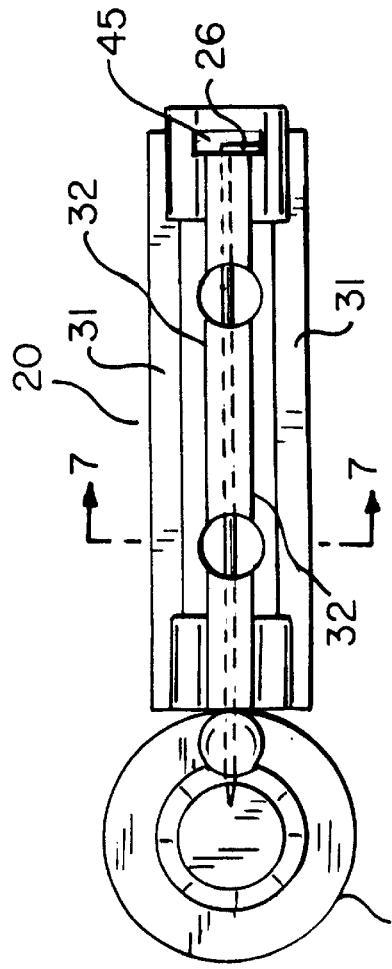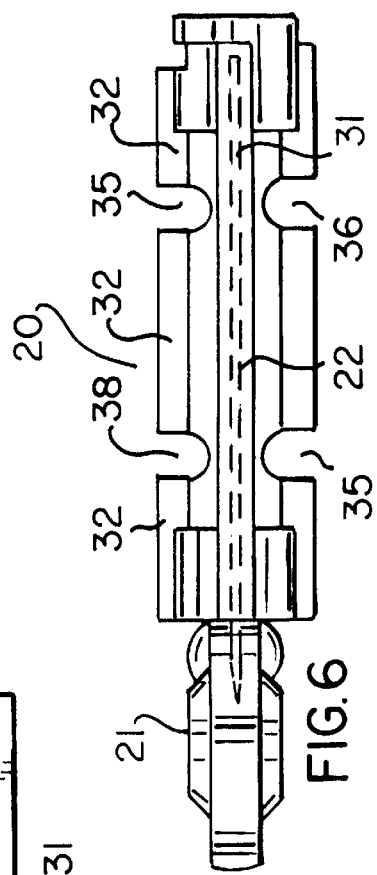

LANCET NEEDLE ANCHOR METHOD

RELATED APPLICATION

This Application is a Divisional of U.S. patent application Ser. No. 10/223,141, filed Aug. 19, 2002, now U.S. Pat. No. 6,589,261.

FIELD OF THE INVENTION

The present invention relates to lancets which are lancing devices primarily used to obtain capillary blood samples for various testing purposes, not the least of which is blood glucose in the case of diabetics where such testing may be done on a daily basis. The purpose of the lancet is to penetrate the epidermis to a sufficient depth in order to draw the necessary amount of blood needed for the test, and yet hold the penetration, scaring, and injury to the epidermis to the irreducible minimum.

BACKGROUND OF THE INVENTION

The present invention has, by way of background, various lancing devices which hold the lancet needle, cover, and carrier. One such device is manufactured for ProCare LLC, and is submitted separately in a prior art disclosure. Basically, however, the lancing device contains a sliding barrel with a trigger button and a base support for the lancet. A lancet cover is provided which threadedly surrounds the lancet as it is positioned in the barrel. At the outer end is an adjustable comfort tip with a lancet cover having numerical indicia and an arrow which, by rotation of the cover, determines the empirical depth to which the needle will penetrate.

Virtually all hypodermic syringes have siliconized needles to aid in insertion to reduce the pain of insertion and further penetration. Therefore, it is desirable to siliconize the lancet needle. This permits the needle to be easily dislodged from the lancet body. In addition, a significant amount of plastic is employed by the prior art for such devices to attempt to secure the needle or blade against dislodgement, and protect against dimensional irregularities.

Therefore, what is needed is a lancet in which the needle portion is firmly embedded in the plastic body, secured against rotation, secured against linear removal, and yet permits the utilization of a minimal amount of plastic, which plastic may be of an inferior grade and therefore less expensive than most lancet bodies, while still providing the sanitary and dimensional support necessary.

SUMMARY OF THE INVENTION

The present invention derives from the molding of a lancet body around a needle or blade, in which the inner end of the needle body which is unsharpened has an L-shape bend. As a result of the L-shape bend, when embedded in the plastic which forms the body of the lancet, the needle can neither rotate nor be removed linearly. In short, the needle is permanently immobilized against movement within the body of the lancet, within the X, Y and Z directions. The method of the present invention involves the bending substantially perpendicularly of the unsharpened end of the needle or blade to be substantially perpendicular with the elongate body of the blade. The thus formed needle or blade is placed within a jig interiorly of the plastic mold which is used to form the lancet body and the cover, with the cover surrounding the entirety of the sharpened portion of the needle or blade. The jig includes spaced opposed clamps and a single orienting support to the bent portion of the needle.

Also, the body of the lancet is relieved in many areas and has a molded tab cover thereby reducing the plastic used and eliminating a loose part such as a separate cover.

In view of the foregoing it is a principal object of the present invention to provide an apparatus and method for forming a lancet in which the needle or blade is securely positioned against any dislodgement, whether by rotation, or by linear movement within the lancet body.

A further object of the present invention is to provide such a lancet in which rotation and longitudinal dislodgement are prevented, which can accommodate a relatively low grade form of plastic and yet present in operation a dimensionally stable lancet, fully sanitary, for use with the typical user's home care kit.

A further object of the present invention is addressed to a method of forming a lancet body and needle or blade with a cover head on a highly cost effective basis attributable to the lack of necessity for special purpose jigs to control the position of the needle or blade within the lancet body. As a result, a further objective is achieved by providing the bent leg or L-shaped end portion so that it can be precisely positioned interiorly in the mold, and the plastic body of the lancet molded around the needle or blade with the offset anchor resulting in a product which is dimensionally accurate to tolerances which are acceptable and heretofore unknown on the quantities produced for the disposable lancet market.

DESCRIPTION OF ILLUSTRATIVE EMBODIMENTS

Further objects and advantages of the present invention will become apparent as the following description proceeds, taken in conjunction with the accompanying illustrative drawings in which:

FIGS. 4A and 4B are two views of the lancet needle which is molded into the body portion of the lancet;

FIG. 5 is a front elevation of the lancet;

FIG. 6 is a side elevation of the lancet;

Figure 8:
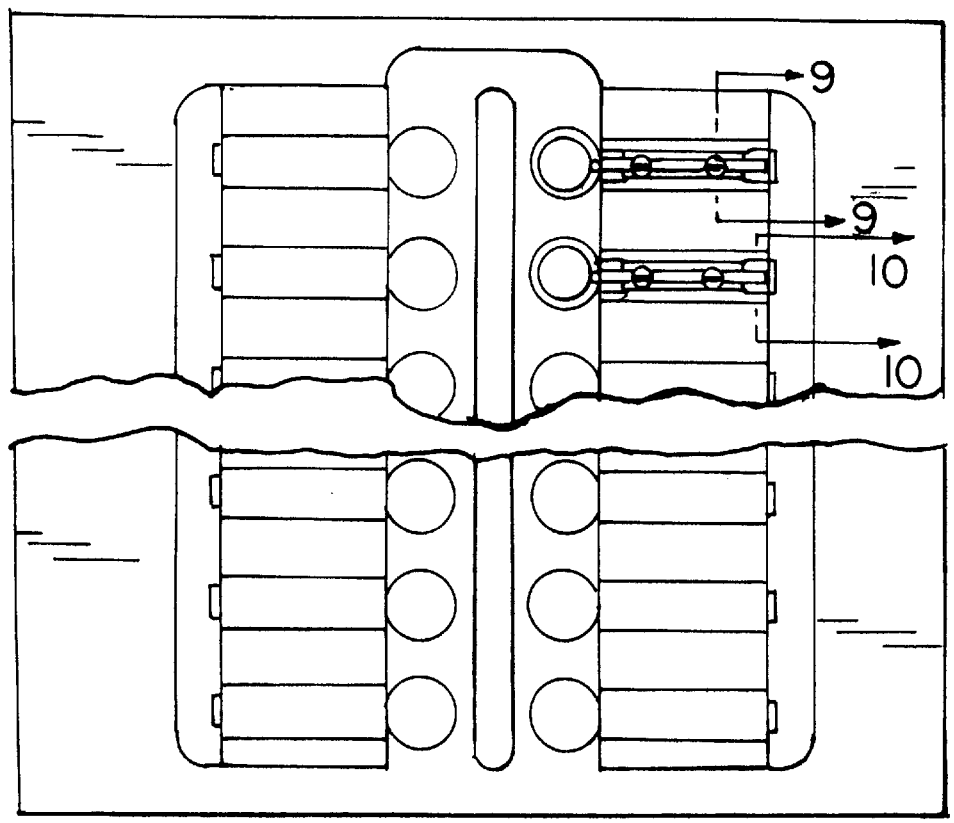
FIG. 8 is a plan view, partially diagrammatic and partially broken, of the lower portion of the mold utilized to form the subject lancet.
Figure 9:
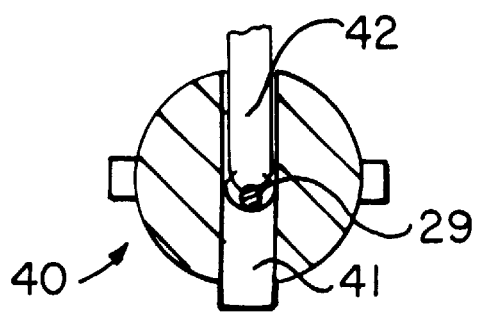
Figure 10:
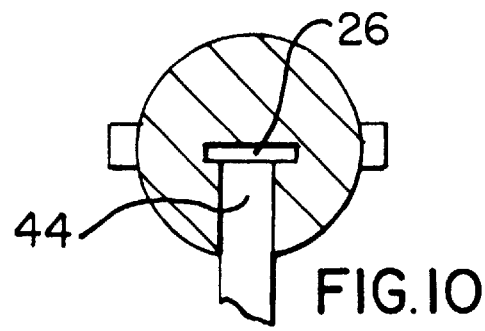

FIG. 9 is a transverse sectional partially diagrammatic view, in enlarged scale, taken along section line 9—9 of FIG. 8; and FIG. 10 is yet another transverse sectional view taken from FIG. 8 at section line 10—10 showing the support for the angled base anchor 26 of the needle 25.

DESCRIPTION OF THE PREFERRED EMBODIMENT

Figure 1:
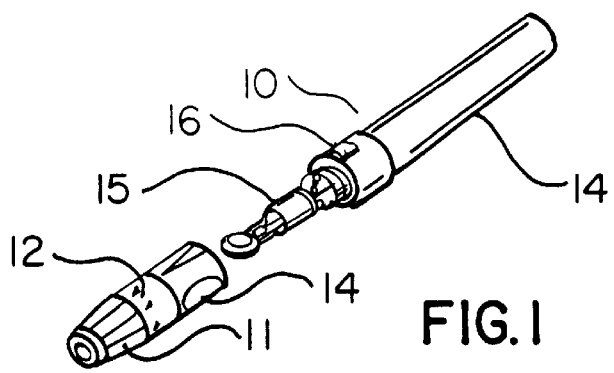
FIG. 1 is an exploded partially perspective view of a typical home lancing device showing the lancet in a mid-portion of the figure.
Figure 2A:
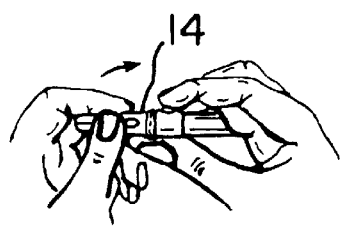
FIGS. 2A, 2B, 2C, 2D, 2E, 2F and 2G, show the utilization of the device typically by the patient applying the lancet to his/her own finger.
Figure 2D:
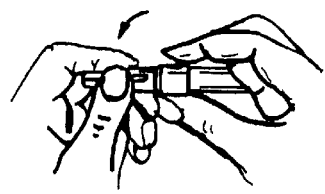
Figure 2B:
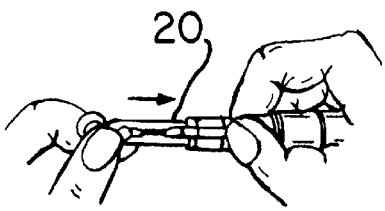
Figure 2E:
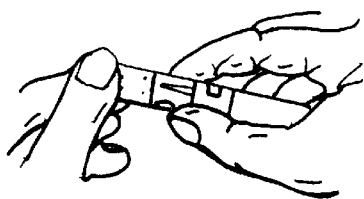
Figure 2C:
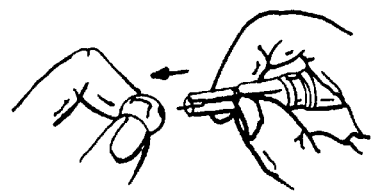
Figure 2F:
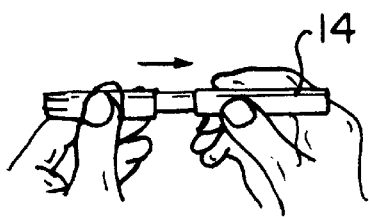
Figure 2G:
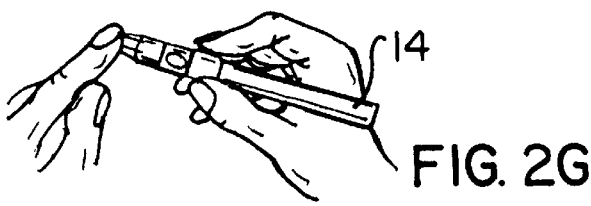

In the preferred embodiment, as illustrated in FIG. 1, the lancing device 10 is used to obtain a capillary blood sample needed for blood glucose monitoring or for other tests requiring one or two drops of blood. The adjustable comfort tip 11 on the lancing device 10 permits choosing the best depth for skin penetration. As shown, there are five discrete positions 12 which can be utilized by the self-user.

As shown in FIGS. 2A through 2G, the needle cover 21 is twisted off of the lancet device 10, the new lancet 20 is thereafter inserted into the lancet carrier 15, the needle cover 21 is removed thereafter revealing the needle 25, the lancet lancing device then has the comfort tip 11 placed in position. At this point, rotation of the adjustable comfort tip 11 offers a plurality of levels of skin penetration (see FIG. 2E). The user empirically determines which of these is best for his use.

The lancing device 10 is cocked by slowly pulling the slide barrel 14 away from the lancing device cover. A click indicates audibly when the carrier is locked in position. Thereafter the end of the adjustable comfort tip is pressed against the finger, the trigger button 16 is engaged, and the lancing device needle tip sharpened end 28 penetrates the epidermis to a point where the one or two drops of blood needed can be drawn.

Figure 3:
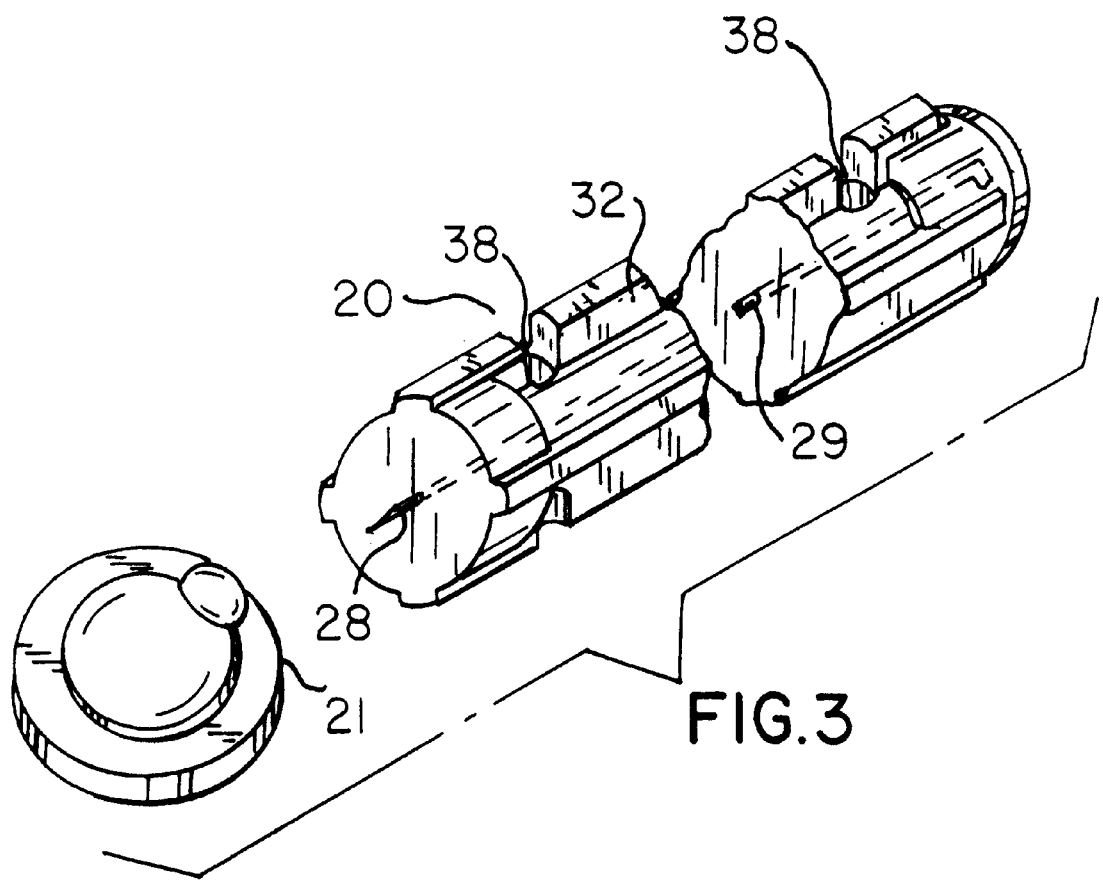
FIG. 3 is a perspective partially broken exploded view of the subject lancet showing the needle or blade interiorly thereof in its secured position.

Turning now to FIG. 3. which is an exploded perspective view, it can be seen that the two principle components of the lancet itself are the body 22 and the needle cover 21 cap which are the molded portions, and the needle or blade 25 which is the metal portion.

Figure 7:
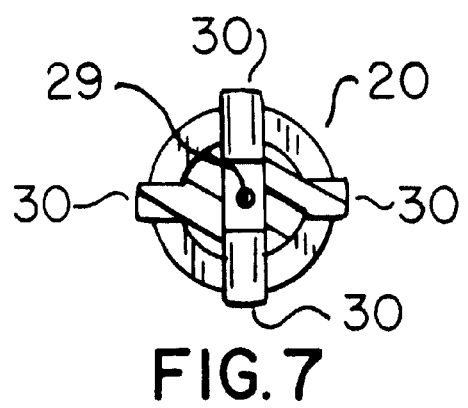
FIG. 7 is a transverse sectional view of the lancet taken at 7—7 of FIG. 5.

Important to the invention, and particularly shown in FIGS. 3, 5 and 8, is the configuration of the needle or blade 25 in which the end opposite the sharpened end 28 has been bent at an angle with the needle body 29. Desirably the bend is perpendicular to the main body 29. Such a bend to form an anchor 26 critical to the present invention in that, by providing the offset, once the needle is molded into the body of the lancet it cannot be moved longitudinally, nor can it be rotated, nor can it be moved sideways in any direction. By virtue of the angled base anchor 26, the needle or blade 25 is permanently, dimensionally and sanitarily positioned inside the lancet body with the needle cover in place but removable by twisting to dislodge, basically as described in FIG. 3 above. The method of the present invention will become more apparent as the description of the body 22 of the lancet proceeds. As can be seen in FIGS. 5 and 6, there are four runners 30 which, in cross-section, give a cruciform appearance, as shown in FIG. 7. There are two uninterrupted runners 31, and two interrupted runners 32. The interrupted runners 32 are formed when the opposed prongs of a vise are positioned in place interiorly of the mold to securely engage the needle prior to injecting the plastic. In this fashion the position of the needle is ensured and when the vise elements are withdrawn from the body 22, ports are revealed which reduce the amount of plastic employed, and simultaneously permit the user to see and observe the needle interiorly of the body 22.

While dimensions and composition materials do not form a key portion of the invention, those used in a commercial embodiment are illustrative of successful dimensions. All dimensions are in millimeters. As noticed particularly in FIGS. 5, and 6 the entire lancet is 32 mm in length. The body portion is 20.7 mm, plus or minus 2 mm. The thickness dimension, taken from the tips of the runners, is 6.3 mm.

The needle, as shown in FIGS. 4A and 4B, is 24.4 mm in length, plus or minus 2 mm. The bent leg is 1.8 mm in length taken from the far side of the body portion. As shown in FIG. 4A, there is double-bevel at the sharpened end 28 of the needle. The material ideally employed is stainless steel 1CR18NI9.

The material employed for the plastic body is LDPE, better known as "low density polyethylene" blended with HDPE, better known as "high density polyethylene". Virgin or reground may be used. Runners and flashing are reground and may be used exclusively or blended with virgin material.

While dimensions are not considered critical, they illustrate the precision involved. The total overall length of the lancet, including the cover, is 32 mm. The diameter at the largest portion of the body across the top of opposed runners is 6 mm. The total diameter of the tip or cap portion is 9.4 mm, and its thickness is 3.5 mm.

THE METHOD

The method of the present invention involves developing a mold for a plurality of needles 25 in connection with a multiple cavity mold in which the needle or blade are positioned so that the same can be an interior portion of the completed lancet 20 when the plastic is injected into the recess which surrounds the carrying portion of the bent angle needle or blade. In this connection, it will be seen in FIG. 5 that the needle body 22 actually shows interiorly of the lancet body 20 because the support which holds the needle is surrounded by plastic, when the support is removed the needle appears. On the opposite side the needle is similarly viewed through much smaller ports. The reason for the smaller ports is that they contain a pin which engages the needle on the post support of the jig interiorly of the mold to thereby firmly position the needle to be encapsulated in the plastic which is thereafter molded around the needle or blade.

Specifically as shown in FIG. 8, a multiple cavity mold is intended for forming the lancet 20. As shown here there are 20 cavities, ten on each side. Specific details of two cavities are shown in the upper right corner of FIG. 8. Turning now to FIG. 9, it will be seen that a clamping assembly 40 is used to engage the main body 29 of the needle 25. The lower jaw 41 of the clamping assembly 40 is somewhat larger than the upper jaw 42 of the same clamping assembly. The needle 25 is positioned on top of the lower jaw 41 prior to molding. At or about the same time, the angled base anchor 26 of the needle 25 is positioned on top of the anchor support 44. When the upper portion of the mold is placed over the lower portion, and the plastic is injected, the needle 25 and its components are securely held in place by the clamping assembly 40. After the plastic has sufficiently cooled, the two mold supports are removed and the lancets 20 removed from the mold. Specifically as shown in FIG. 5, it will be seen that the interrupted runners 32 have ports which remain exposing needle body. The vise ports 35 are large vise ports 36, and small vise ports 38. In addition, there is an anchor support port 45, viewed particularly in FIG. 5, and in which the angled base anchor 26 of the needle 25 is exposed. This results from the withdrawal of the anchor support 44 when the upper and lower portions of the mold are separated.

Summarizing the above, the method contemplates providing a mold having a plurality of cavities which are the mirror image of the lancet 20 to be molded. The next step in the process relates to providing clamping means, which are opposed, and which clampingly engage the needle body at spaced relationship. Finally, the step includes providing an anchor support at one end whereby the needle is not only supported on the anchor, but the anchor determines the position of the point of the needle within the molded lancet body cover. Thus, the sequencing, once the clamping means are provided within the mold, and the support means exist for the angled base anchor portion 26 of the needle 25, the needles are inserted in the one portion of the mold on top of their respective supports, shown here as three in number (two for the needle body 25 and one for the angled base anchor 26). Thereafter the mold top is placed on the mold bottom, the clamping members engage the needle 25 in fixed relationship to the cavity to be filled with plastic. Once the plastic is within the balance of the cavity, the needle is positively oriented therein in relation to the base of the needle and the runners which, in turn, control the spaced relationship of the sharpened end 28 of the needle or blade 25 when positioned in a typical lancing device 10, such as shown in FIGS. 1 and 2A through 2G.

It will be understood that various changes in the details, materials and arrangements of parts, or method which have been herein described and illustrated in order to explain the nature of the invention, may be made by those skilled in the art within the principle and scope of the invention as expressed in the appended claims.

What is claimed is:

1. A method of forming a lancet having a needle or blade within an elongate lancet body, produced in accordance with the following steps:

bending one end of said needle or blade, and sharpening the other end to form a point;

forming a mold for the lancet body which forms a cavity complementary to the shape the lancet body including forming a cap portion to encapsulate the sharpened end of the needle or blade;

providing opposed clamping members at an interior portion of the mold in vise-like relationship to the needle or blade;

injecting plastic into the mold after the needle or blade has been positioned therein; and thereafter opening the mold and removing the lancet; whereby the needle or blade is sanitarily housed within the lancet body with the needle or blade point encapsulated in the head and revealing, through the recesses in the lancet body left by the withdrawal of the jig, opposite sides of the needle or blade.

2. A method of forming a lancet having a needle or blade within a lancet body, including the steps of:

a) providing a needle or blade having a first sharpened end and a second end remote from said first end;

b) providing a bend in said needle or blade remote from said first end;

c) providing a mold with at least one cavity configured to create said lancet body;

d) clamping said needle or blade within said at least one cavity with a clamp engaging said needle or blade from opposed sides thereof;

e) injecting plastic into said mold, said plastic encapsulating said bend and surrounding said clamp;

f) removing said lancet.

3. The method of claim 2, during said removing step, further including the step of unclamping said clamp to create opposed holes in said needle or blade to view.

4. The method of claim 2, wherein said clamp includes opposed clamping members.

5. The method of claim 4, wherein one of said clamping members has a concave end surface and another of said clamping members has a convex end surface.

6. The method of claim 5, wherein said clamping member with said concave end surface has a larger diameter than a diameter of said another of said clamping members.

7. The method of claim 2, further including the step of providing said mold cavity with a region adapted to mold a cap portion for said sharpened end of said needle on blade.

8. The method of claim 2, wherein said at least one cavity comprises a plurality of cavities and further including the step of simultaneously molding a plurality of lancet bodies.

9. The method of claims 8, wherein said clamp includes opposed clamping members.

10. The method of claim 9, wherein one of said clamping members has a concave end surface and another of said clamping members has a convex end surface.

11. The method of claim 2, further including the step of providing said cavity with a support for said bend.

12. The method of claim 11, wherein said bend is at said second end of said needle or blade.

13. A method of forming a lancet having a needle or blade within a lancet body, including the steps of:

a) providing a needle or blade having a first sharpened end and a second end remote from said first end;

b) providing a bend in said needle or blade at said second end;

c) providing a mold with at least one cavity configured to create said lancet body;

d) clamping said needle of blade within said at least one cavity with a clamp engaging said needle or blade from opposed sides thereof;

e) removing said lancet and unclamping said clamp to create opposed holes in said lancet body exposing said needle or blade to view.

14. The method of claim 13, wherein said clamp includes opposed clamping members.

15. The method of claim 14, wherein one of said clamping members has a concave end surface and another of said clamping members has a convex end surface.

16. The method of claim 15, wherein said clamping member with said concave end surface has a larger, diameter than a diameter of said another of said clamping members.

17. The method of claim 13, further including the step of providing said mold cavity with a region adapted to mold a cap portion for said sharpened end of said needle or blade.

18. The method of claim 13, wherein said at least one cavity comprises a plurality of cavities and further including the step of simultaneously molding a plurality of lancet bodies.

19. The method of claim 13, further including the step of providing said cavity with a support for said bend.

* * * * *